(12) United States Patent
Phadke et al.

(10) Patent No.: US 9,481,708 B2
(45) Date of Patent: Nov. 1, 2016

(54) PROCESS FOR PRODUCING SOVAPREVIR

(71) Applicant: Achillion Pharmaceuticals, Inc., New Haven, CT (US)

(72) Inventors: Avinash Phadke, Branford, CT (US); Akihiro Hashimoto, Branford, CT (US); Venkat Gadhachanda, Hamden, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 0 days.

(21) Appl. No.: 14/803,234

(22) Filed: Jul. 20, 2015

(65) Prior Publication Data

US 2015/0322109 A1 Nov. 12, 2015

Related U.S. Application Data

(62) Division of application No. 14/211,510, filed on Mar. 14, 2014, now Pat. No. 9,115,175.

(60) Provisional application No. 61/784,182, filed on Mar. 14, 2013.

(51) Int. Cl.
*C07D 401/12* (2006.01)
*C07K 5/078* (2006.01)
(Continued)

(52) U.S. Cl.
CPC ......... *C07K 5/06139* (2013.01); *C07D 207/16* (2013.01); *C07D 401/06* (2013.01); *C07D 401/12* (2013.01); *C07D 401/14* (2013.01); *C07K 5/0821* (2013.01); *C07B 2200/13* (2013.01)

(58) Field of Classification Search
None
See application file for complete search history.

(56) References Cited

U.S. PATENT DOCUMENTS 6,872,805 B2    3/2005    Campbell et al.
6,908,901 B2    6/2005    Bailey et al.
(Continued)

FOREIGN PATENT DOCUMENTS

WO    02060926 A2    8/2002
WO    03099274 A1    12/2003
(Continued)

OTHER PUBLICATIONS

Andrews et al.., "Pyrrodlidine-5, 5-trans-lactams. 2. The Use of X-ray Crystal Stucture Date in the Optimization of P3 and P4 Substituents" Organic Letters, vol. 4, No. 25, (2002), pp. 4479-4482.
(Continued)

*Primary Examiner* — Thomas S Heard
(74) *Attorney, Agent, or Firm* — Knowles IP Strategies, LLC

(57) ABSTRACT

The disclosure includes novel processes for producing Sovaprevir comprising adding

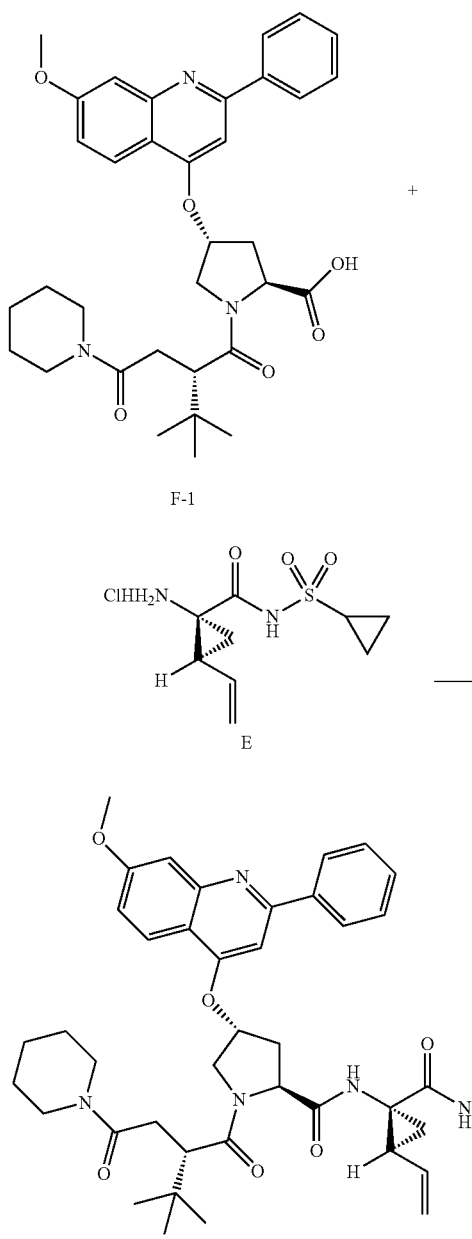

compound E to F-1 to provide Sovaprevir. The disclosure further includes intermediates useful for producing Sovaprevir. The disclosure also include a novel crystalline form of Sovaprevir, Form F, and a method for preparing spray-dried amorphous Sovaprevir from crystalline Form F.

5 Claims, 4 Drawing Sheets

(51) Int. Cl.
*C07K 5/097* (2006.01)
*C07D 207/16* (2006.01)
*C07D 401/06* (2006.01)
*C07D 401/14* (2006.01)

(56) References Cited

U.S. PATENT DOCUMENTS

| | | | |
|---|---|---|---|
| 6,995,174 B2 | 2/2006 | Wang et al. | |
| 7,041,698 B2 | 5/2006 | Ripka et al. | |
| 7,176,208 B2 | 2/2007 | Nakajima et al. | |
| 9,133,115 B2* | 9/2015 | Phadke | C07D 207/16 |
| 2004/0002448 A1 | 1/2004 | Tsantrizos et al. | |
| 2004/0048802 A1 | 3/2004 | Ripka et al. | |
| 2004/0077551 A1 | 4/2004 | Campbell et al. | |
| 2004/0224900 A1 | 11/2004 | Bailey et al. | |
| 2006/0019905 A1 | 1/2006 | Bailey et al. | |
| 2006/0046965 A1 | 3/2006 | Bailey et al. | |
| 2006/0199773 A1 | 9/2006 | Sausker et al. | |
| 2007/0010455 A1 | 1/2007 | Hewawasam et al. | |
| 2007/0093414 A1 | 4/2007 | Carini et al. | |
| 2007/0099825 A1 | 5/2007 | D'Andrea et al. | |
| 2010/0216725 A1 | 8/2010 | Phadke et al. | |

FOREIGN PATENT DOCUMENTS

| | | |
|---|---|---|
| WO | 03099316 A1 | 12/2003 |
| WO | 2004043339 A2 | 5/2004 |
| WO | 2004072243 A2 | 8/2004 |
| WO | 2004094452 A2 | 11/2004 |
| WO | 2004103996 A1 | 12/2004 |
| WO | 2004113365 A2 | 12/2004 |
| WO | 2005007681 A2 | 1/2005 |
| WO | 2005028501 A1 | 3/2005 |
| WO | 2005037214 A2 | 4/2005 |
| WO | 2005046712 A1 | 5/2005 |
| WO | 2005051410 A1 | 6/2005 |
| WO | 2005054430 A2 | 6/2005 |
| WO | 2005070955 A1 | 8/2005 |
| WO | 2005073216 A1 | 8/2005 |
| WO | 2005090383 A2 | 9/2005 |
| WO | 2005095403 A2 | 10/2005 |
| WO | 2006007700 A1 | 1/2006 |
| WO | 2006007708 A1 | 1/2006 |
| WO | 2006033878 A1 | 3/2006 |
| WO | 2006086381 A2 | 8/2006 |
| WO | 2006096652 A2 | 9/2006 |
| WO | 2007005838 A1 | 1/2007 |
| WO | 2007009109 A2 | 1/2007 |
| WO | 2007009227 A1 | 1/2007 |
| WO | 2007014919 A1 | 2/2007 |
| WO | 2007015824 A2 | 2/2007 |
| WO | 2007030656 A1 | 3/2007 |
| WO | 2007044893 A2 | 4/2007 |
| WO | 2008008502 A1 | 1/2008 |

OTHER PUBLICATIONS

Arasappan et al.., "Hepatitis C Virus NS3-4A Serine Protease Inhibitors: SAR of P2 Moeity with Improved Potency" Bioorganic and Medicinal Chemistry Letters, 15 (2005), pp. 4180-4184.

Barbato et al.., "Inhibitor Binding Induces Active Site Stabilization of the HCV NS3 Protein Serine Protease Domain" The EMBO Journal; vol. 19; No. 6; (2000); pp. 1195-1206.

Di Marco et al.., "Inhibtion of the Hepatitis C Virus NS3/4A Protease" The Journal of Biological Chemistry, vol. 275, No. 10, Issue of Mar. 10, 2000, pp. 7152-7157.

International Search Report of the International Searching Authority for Internatitonal Application No. PCT/US2007/016018; International Filing Date: Jul. 13, 2007; Date of Mailing: Dec. 12, 2007, 14 Pages.

International Search Report of the International Searching Authority for Internatitonal Application No. PCT/US2014/028278, International Filing Date: Mar. 14, 2014; Date of Mailing: Nov. 10, 2014; 6 Pages.

Liu et al.., "Hepatitis C NS3 Protease Inhibition by Peptidyl-a-Ketoamide Inhibitors: Kinetic Mechanism and Structure" Archives of Biochemistry and Biophysics, 421, (2004), pp. 207-216.

Ontoria et al.., "The Design and Enzyme-Bound Crystal Structure of Indoline Based Peptidomimetic Inhibitors of Hepatitis C Virus NS3 Protease" Journal of Med. Chem.., 47, (2004), pp. 6443-6446.

Slater et al.., "Pyrrolidine-5,5-Trans-Lactams. 4. Incorporation of a P3/P4 Urea Leads to Potent Intracellular Inhibitors of Hepatitis C Virus NS3/4A Protease" Organic Letters, vol. 5, No. 24, (2003), pp. 4627-4630.

Venkatraman, et al.., "Discovery of (1R,5S)-N-[3-Amino-1-(cyclobutylmethyl)-2,3-dioxopropyl]-3-[2(s)-[[[1,1-dimethyl-lethyl)amino]carbonyl]amino]-3,3-dimethyl-1-oxobutyl]-6,6-dimethyl-3-azabicyclo[3.1.0]hexan-2(S)-carboxamide (SCH 50304), a Selective, Potent, Orally Bioavailable Hepatitis C Virus NS3 Protease Inhibitor: A Potential Therapeutic Agent for the Treatment of Hepatitis C Inflection," J. Med. Chem. 2006, 49; pp. 6074-6086.

Written Opinion of the International Searching Authority for International Application No. PCT/US2007/016018; International Filing Date: Jul. 13, 2007, Date of Mailing: Dec. 12, 2007, 8 Pages.

Written Opinion of the International Searching Authority for International Patent Application No. PCT/US2014/028278; International Filing Date: Mar. 14, 2014, Date of Mailing: Nov. 10, 2014; 9 Pages.

* cited by examiner

PROCESS FOR PRODUCING SOVAPREVIR

CROSS REFERENCE TO RELATED APPLICATION

This application is a divisional of U.S. patent application Ser. No. 14/211,510, filed Mar. 14, 2014, which claims priority from U.S. Provisional Application No. 61/784,182, filed Mar. 14, 2013, which is hereby incorporated by reference in its entirety.

BACKGROUND

Sovaprevir is a hepatitis C virus NS3 protease inhibitor, effective for treating HCV infection in humans.

Sovaprevir can be prepared by the method presented in U.S. Pat. No. 7,906,619, Example 1.

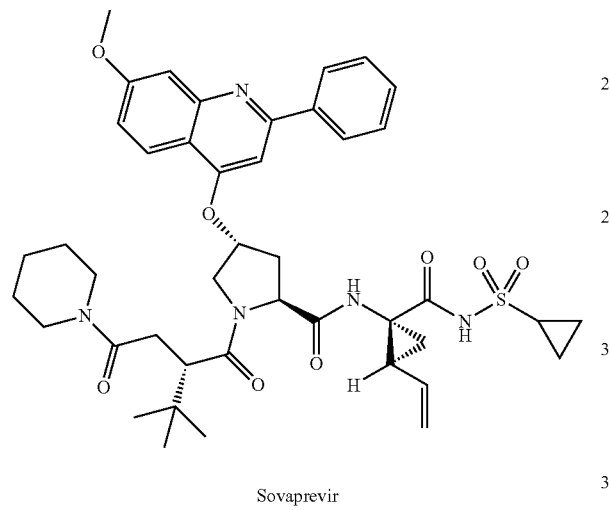

Sovaprevir

SUMMARY

The disclosure provides methods of preparing Sovaprevir. These methods are designated Methods 1 and 2 in the EXAMPLES section of the application. A number of the steps in the methods are unique as are the overall methods for preparing Sovaprevir. The disclosure provides the steps occurring after the synthesis of Compound 13 in synthetic Method 1 to form Sovaprevir. The disclosure also provides the addition of Compound F-1 to Compound E to form Sovaprevir. The formation of the product in Scheme IX, Method 2, (Compound IX) is provided, as is the formation of Sovaprevir from the steps occurring after the formation of the Scheme IX product.

The disclosure also provides intermediates useful for preparing Sovaprevir and close analogues of Sovaprevir. Particularly the disclosure provides, as useful intermediates, at least Compounds 13, 14, 15, C, C-1, and D in Method 1, the compounds of Schemes IX, X, and XI, F, F-1 (the first compound of Scheme XIII in Method 2), and F-2.

The disclosure provides a crystalline polymorph, Form F.

The disclosure further provides a bioavailable amorphous form of Sovaprevir and a method for making the amorphous form.

DETAILED DESCRIPTION

Starting materials for sovaprevir production are prepared by methods known in the art. For example Compound A (tert-butyl((1R)-1-((cyclopropylsulfonyl)carbamoyl)-2-vinylcyclopropyl)carbamate) is prepared by the method discussed in WO 2006/122188, page 34, Scheme III and pages 77-78. This procedure is illustrated in Scheme I.

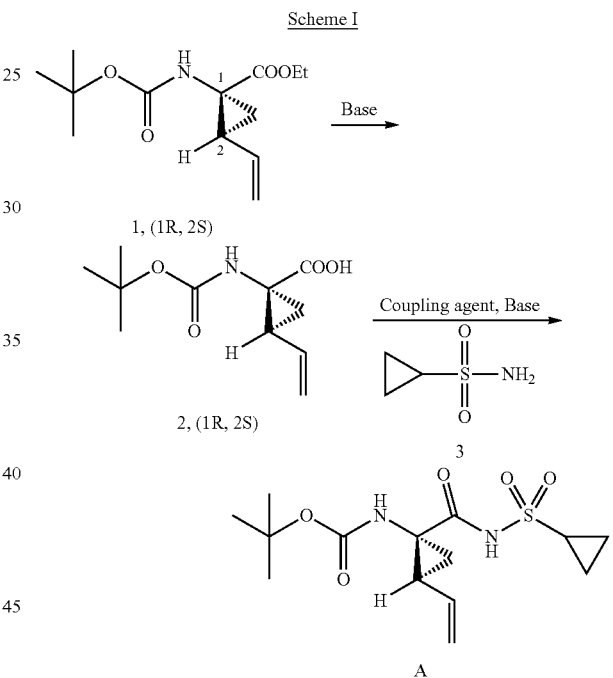

Compound B ((S)-4-(tert-butoxy)-2-(tert-butyl)-4-oxobutanoic acid) is prepared by the method discussed in Evans et. al. *J. Org. Chem.* 1999, 64, 6411-6417. The synthesis of Compound B is shown in Scheme II.

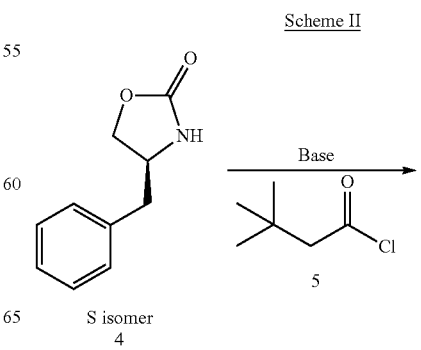

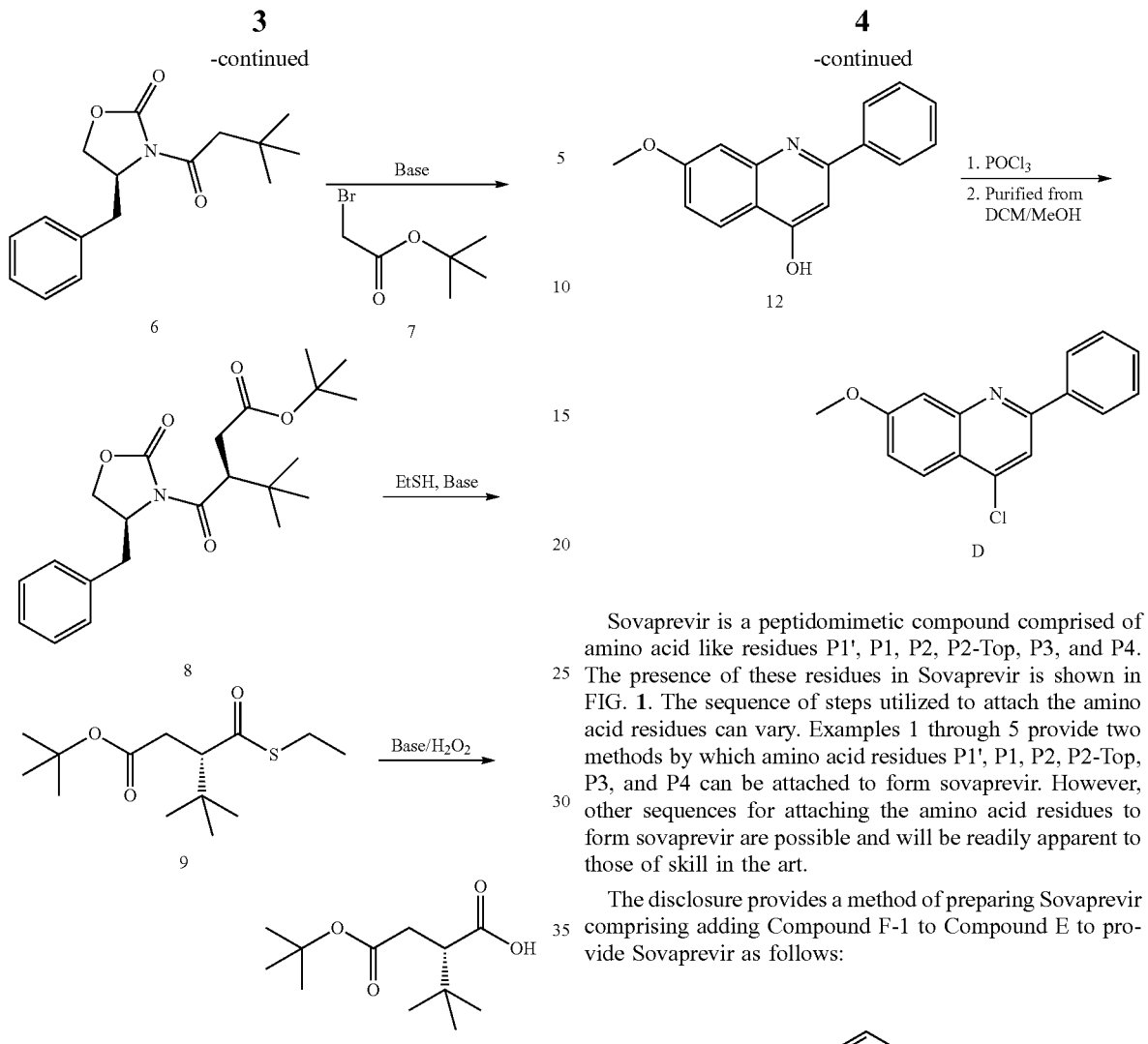

Figure 1:
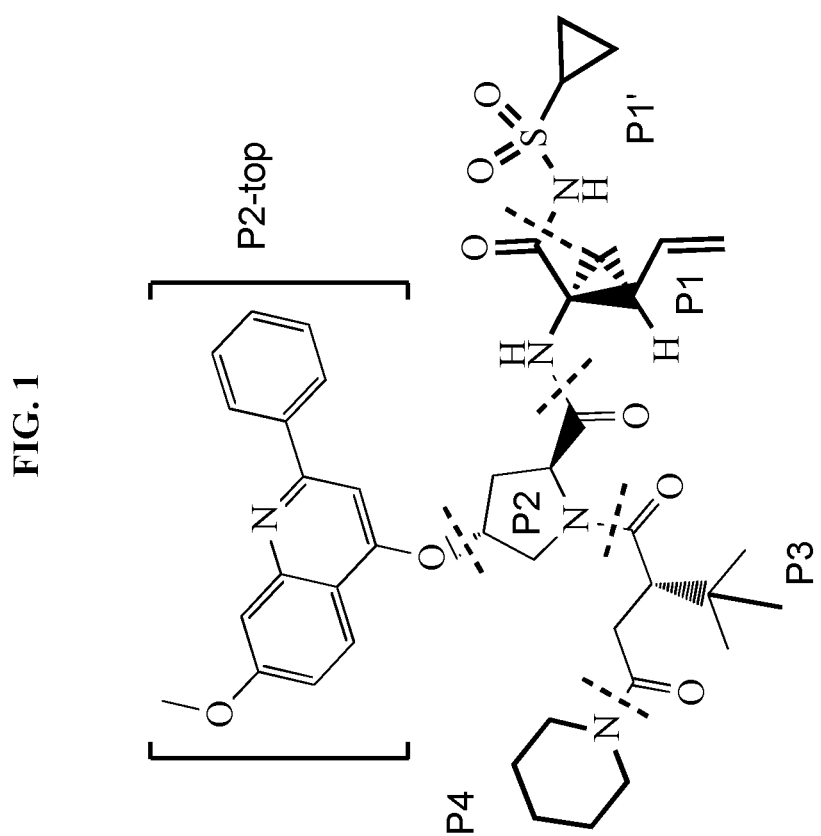
FIG. 1. Amino acids residues P1', P1, P2, P2 Top, P3, and P4 as present in sovaprevir.

Sovaprevir is a peptidomimetic compound comprised of amino acid like residues P1', P1, P2, P2-Top, P3, and P4. The presence of these residues in Sovaprevir is shown in FIG. 1. The sequence of steps utilized to attach the amino acid residues can vary. Examples 1 through 5 provide two methods by which amino acid residues P1', P1, P2, P2-Top, P3, and P4 can be attached to form sovaprevir. However, other sequences for attaching the amino acid residues to form sovaprevir are possible and will be readily apparent to those of skill in the art.

The disclosure provides a method of preparing Sovaprevir comprising adding Compound F-1 to Compound E to provide Sovaprevir as follows:

Compound D (4-chloro-7-methoxy-2-phenylquinoline) is prepared by the method reported in WO 2000/009543, page 51. This method is illustrated in Scheme III

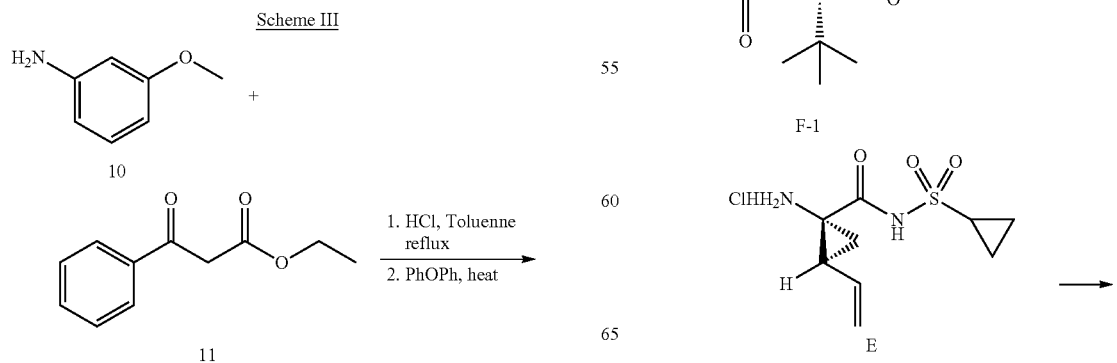

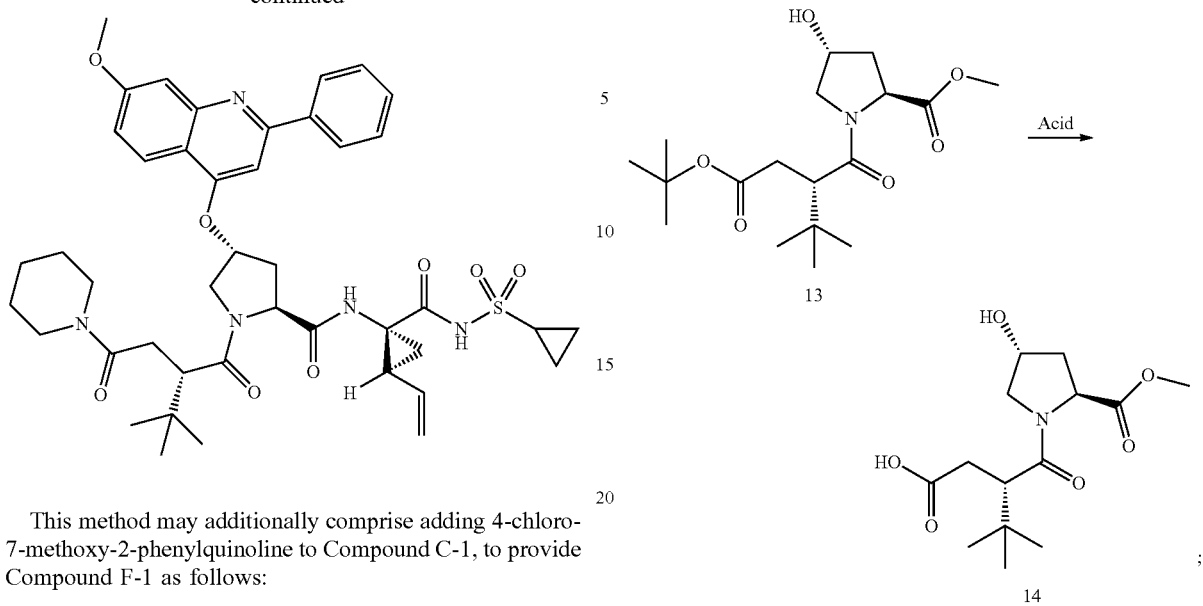

This method may additionally comprise adding 4-chloro-7-methoxy-2-phenylquinoline to Compound C-1, to provide Compound F-1 as follows:

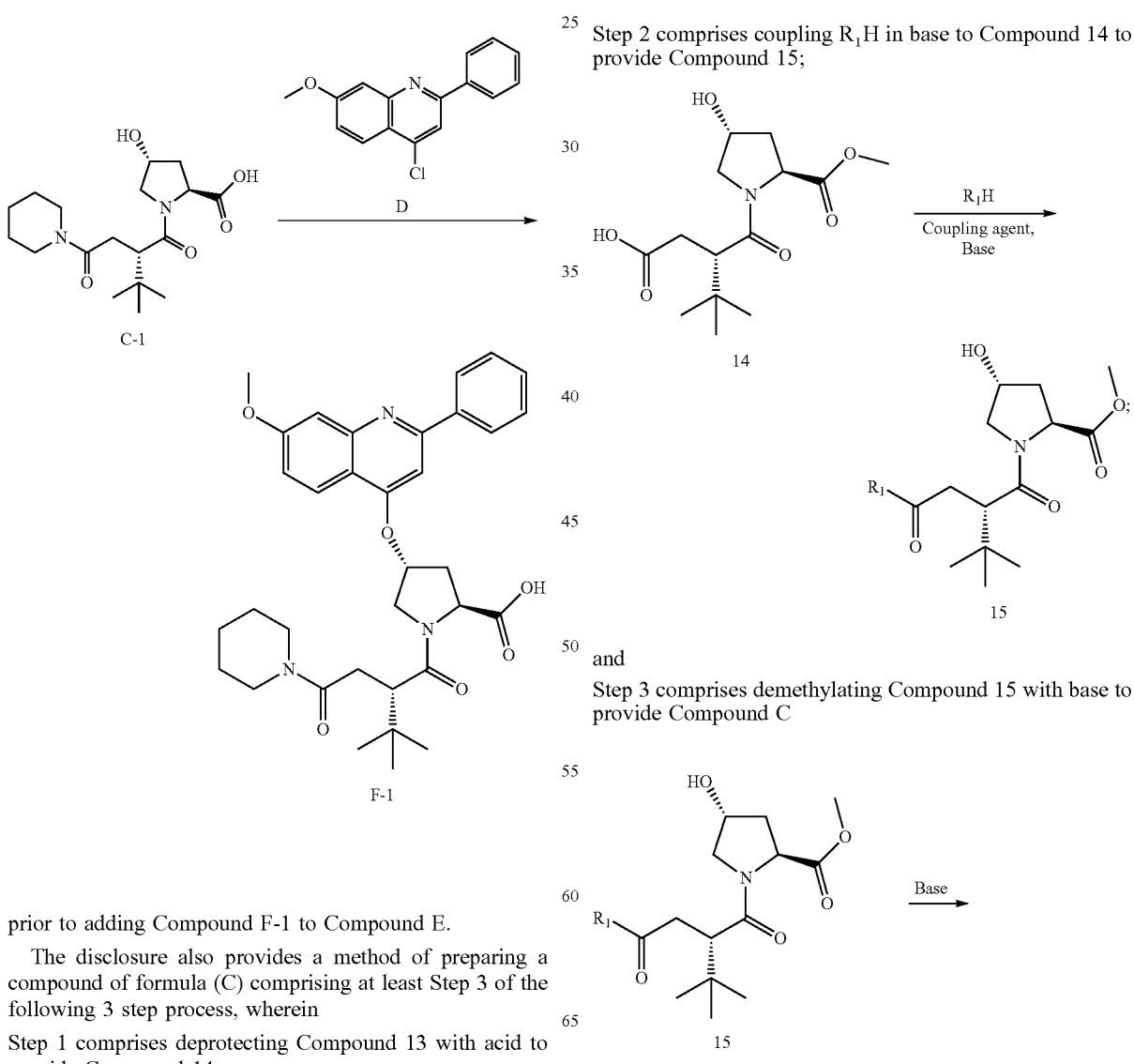

prior to adding Compound F-1 to Compound E.

The disclosure also provides a method of preparing a compound of formula (C) comprising at least Step 3 of the following 3 step process, wherein Step 1 comprises deprotecting Compound 13 with acid to provide Compound 14

Step 2 comprises coupling $R_1H$ in base to Compound 14 to provide Compound 15;

and

Step 3 comprises demethylating Compound 15 with base to provide Compound C

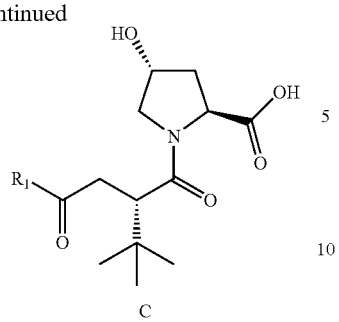

C where R₁ is a Nitrogen bound 4- to 7-membered heterocycloalkyl ring containing 0 to 2 additional heteroatoms independently chosen from N, O, and S which ring is optionally fused to a 5- or 6-membered heterocyclic ring, containing 1 or 2 heteroatoms independently chosen from N, O, and S, or 5- or 6-membered carbocyclic ring to form a bicyclic ring system, each of which 5- to 7-membered heterocycloalkyl ring or bicyclic ring system is optionally substituted with with 0 to 2 substituents independently chosen from fluoro, amino, hydroxyl, methyl, and trifluoromethyl. In certain embodiments R₁ is a 1-piperidinyl, 1-piperazinyl, or 1-pyrrolidinyl group, each of which is unsubstituted or substituted with 1 or 2 halogen substituents. In certain embodiments Step 2 includes coupling piperidine in base. In this case Step 2 comprises coupling piperidin in base to Compound 14 to provide Compound 17;

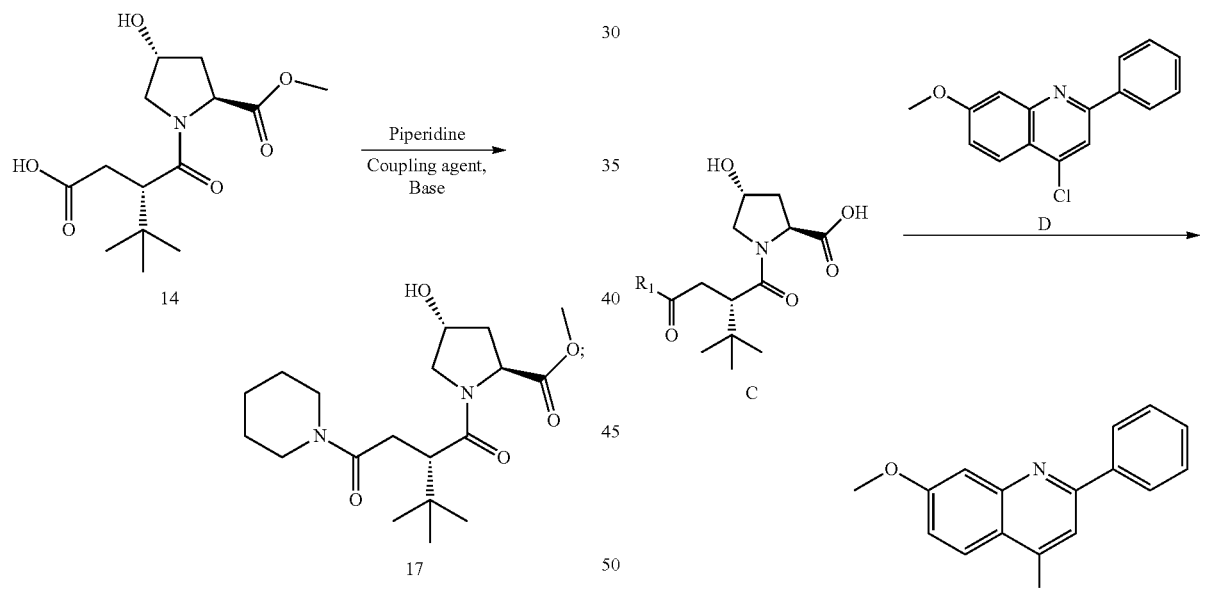

and
Step 3 comprises demethylating Compound 17 with base to provide Compound C-1

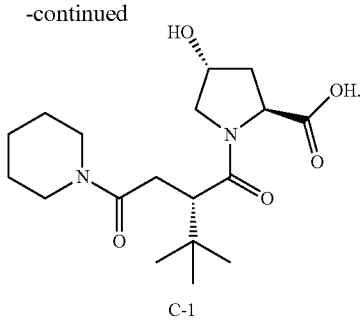

C-1

In certain embodiments R₁ is a 3,3-difluoropiperidin-1-yl group or R₁ is a 1-piperidinyl group.

The disclosure includes the above method for preparing Compound C, comprising Steps 2 and 3 of the method, where R₁ may carry any of the definitions set forth above for this variable.

The disclosure includes the above method for preparing Compound C, comprising Steps 1, 2, and 3 of the method, where R₁ may carry any of the definitions set forth above for this variable.

The disclosure includes a method of preparing Compound F-2, comprising adding 4-chloro-7-methoxy-2-phenylquinoline to Compound C, to provide Compound F-2 as follows:

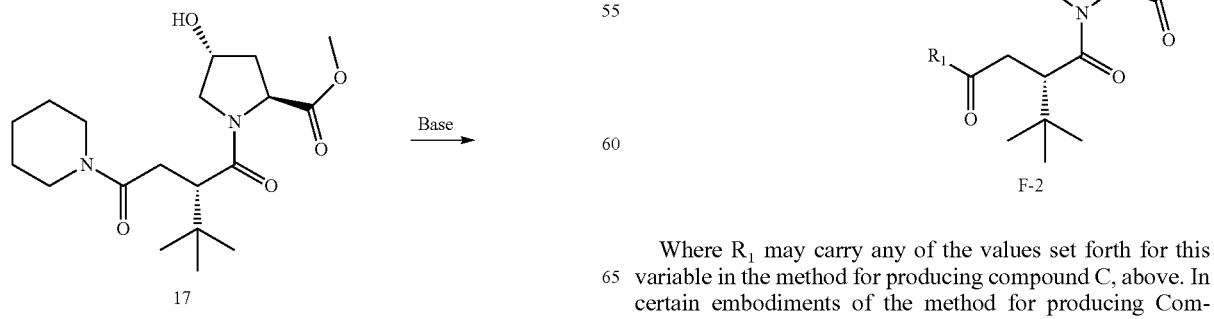

F-2

Where R₁ may carry any of the values set forth for this variable in the method for producing compound C, above. In certain embodiments of the method for producing Compound F-2, R₁ is a 1-piperidinyl, 1-piperazinyl, or 1-pyrrolidinyl group, each of which is unsubstituted or substituted with 1 or 2 halogen substituents, or R₁ is a 1-piperidinyl group.

The disclosure includes an intermediate useful in the processes described in this disclosure, of the Formula C-2

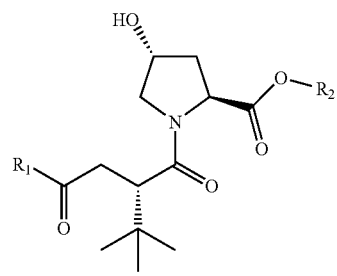

C-2

R₁ in Formula C-2 may carry any of the definitions set forth above. In certain embodiments R₁ is C₁-C₆alkyl or hydroxyl, or R₁ is a 1-piperidinyl, 1-piperazinyl, or 1-pyrrolidinyl group, each of which is unsubstituted or substituted with 1 or 2 halogen substituents; and R₂ is hydrogen or C₁-C₆alkyl, or R₂ is methyl.

The disclosure includes intermediates of Formula C or C-2, in which R₁ is t-butoxy, hydroxyl, or 1-piperidine, and R₂ is methyl.

In certain embodiment the intermediate is a compound of Formula C-1.

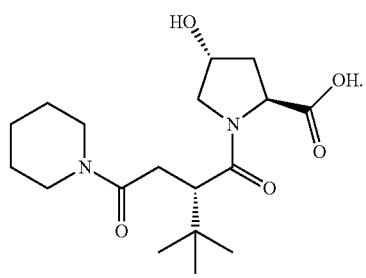

C-1

The disclosure also includes intermediate of Formula F useful for preparing Sovaprevir.

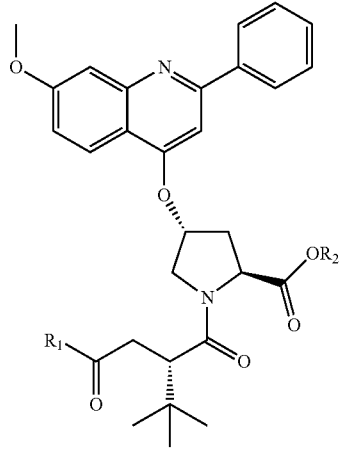

F

R₁ and R₂ in Formula F, may carry any of the definitions set forth above for these variables. In certain embodiments R₁ is a 1-piperidinyl, 1-piperazinyl, or 1-pyrrolidinyl group, each of which is unsubstituted or substituted with 1 or 2 halogen substituents; and R₂ is hydrogen or methyl.

In certain embodiments the intermediate of Formula F is a compound of Formula F-1.

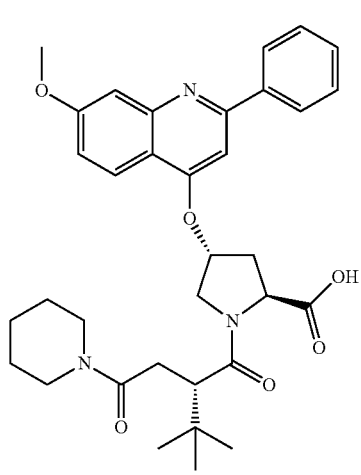

F-1

In other embodiments the disclosure includes compounds having the formula of any of Compounds IX, X, or XI:

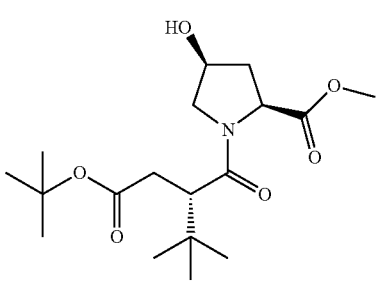

Compound IX

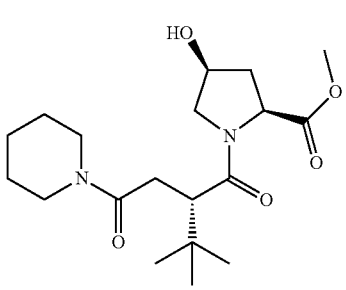

Compound X

-continued

Compound XI

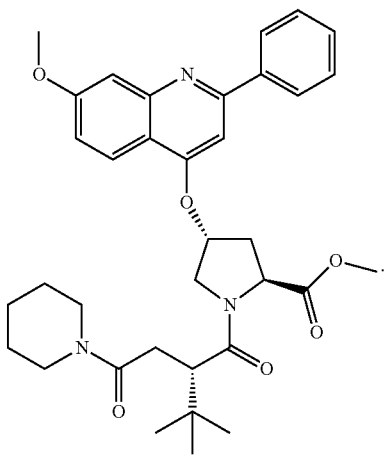

The disclosure includes the method for making Sovaprevir shown above, comprising adding Compound F-1 to Compound E to provide Sovaprevir, and, additionally comprising the step of hydrolyzing the ester in compound XI with base to form F-1 as follows:

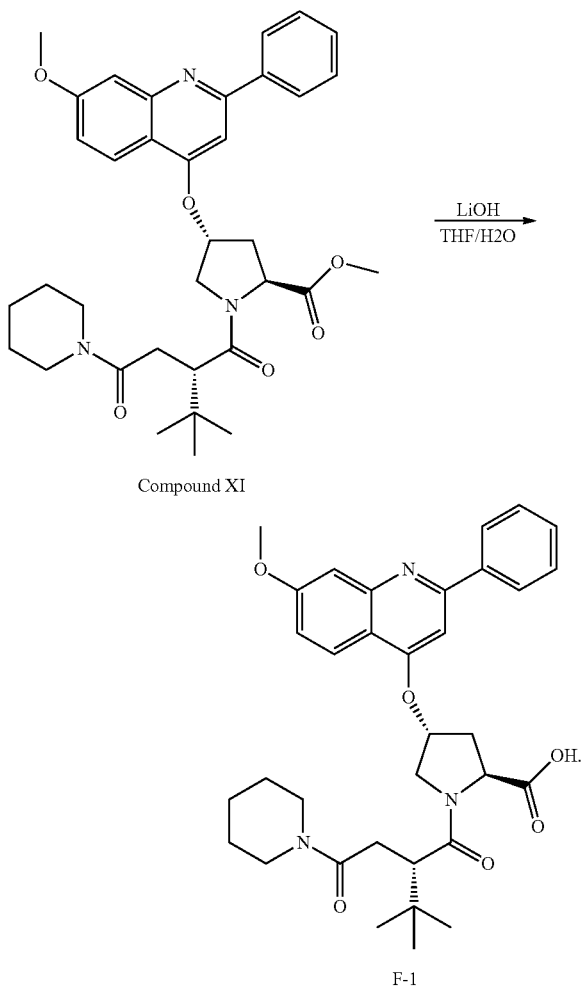

This step is performed prior to adding Compound F-1 to Compound E to provide Sovaprevir.

The disclosure also provides a method of preparing a pure amorphous form of Sovaprevir, comprising: crystallizing Sovaprevir in isopropyl alcohol to form Sovaprevir crystalline Form F in greater than 98% purity; dissolving the Sovaprevir crystalline Form F in 6-12 volumes of a solvent such as acetone; adding 6-13 volumes water relative to volume acetone; and precipitating amorphous Sovaprevir.

The disclosure provides a method of preparing a pure amorphous form of Sovaprevir, comprising crystallizing Sovaprevir in isopropyl alcohol to form Sovaprevir crystalline Form F in greater than 98% purity; dissolving Form F in a solvent such as acetone to form dissolved Sovaprevir; and spray drying the dissolved Sovaprevir to form an amorphous Sovaprevir.

The disclosure provides a crystalline Sovaprevir form, comprising polymorph F.

Figure 2:
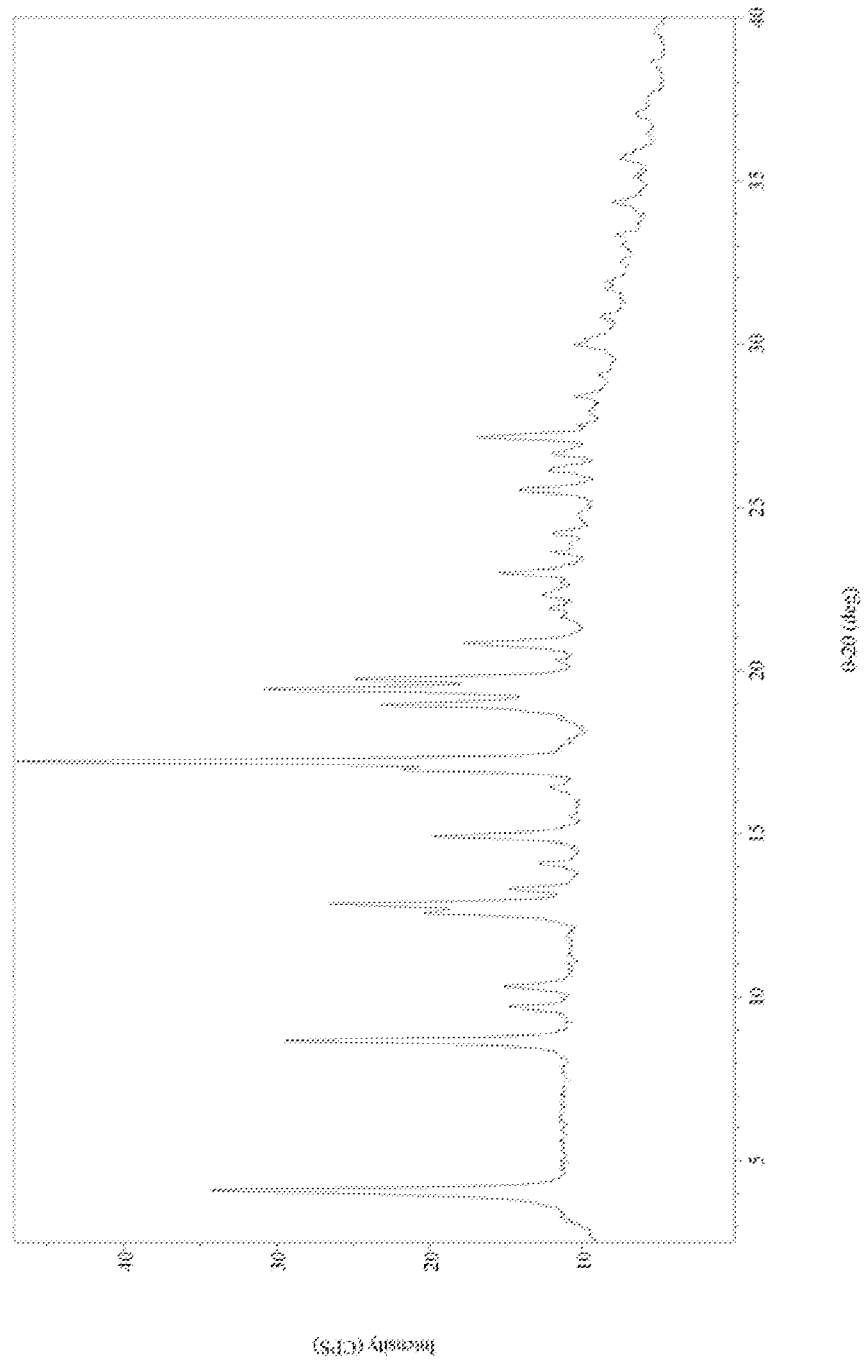
FIG. 2 is a graph of intensity (counts per second, CPS) versus scattering angle (degrees 2θ) showing the results of X-ray powder diffraction analysis of the Form F presented in Example 9.
Figure 3:
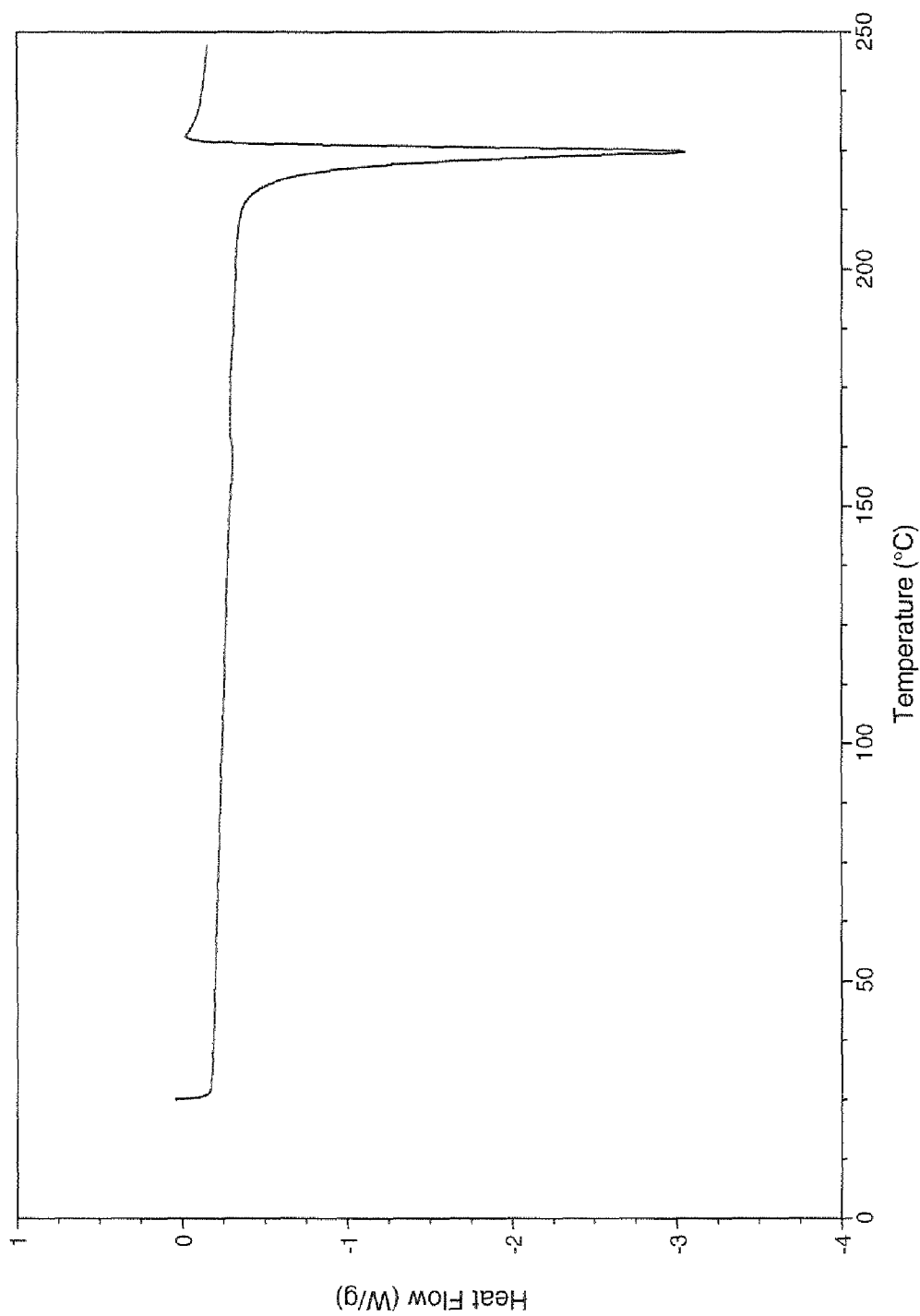
FIG. 3 is a graph of heat flow (Watts per gram, W/g) versus temperature (° C.) showing the results of differential scanning calorimetry analysis of the Form F polymorph, sample size 0.990 mg. Additional experimental details for the DSC analysis are provided in Example 9.
Figure 4:
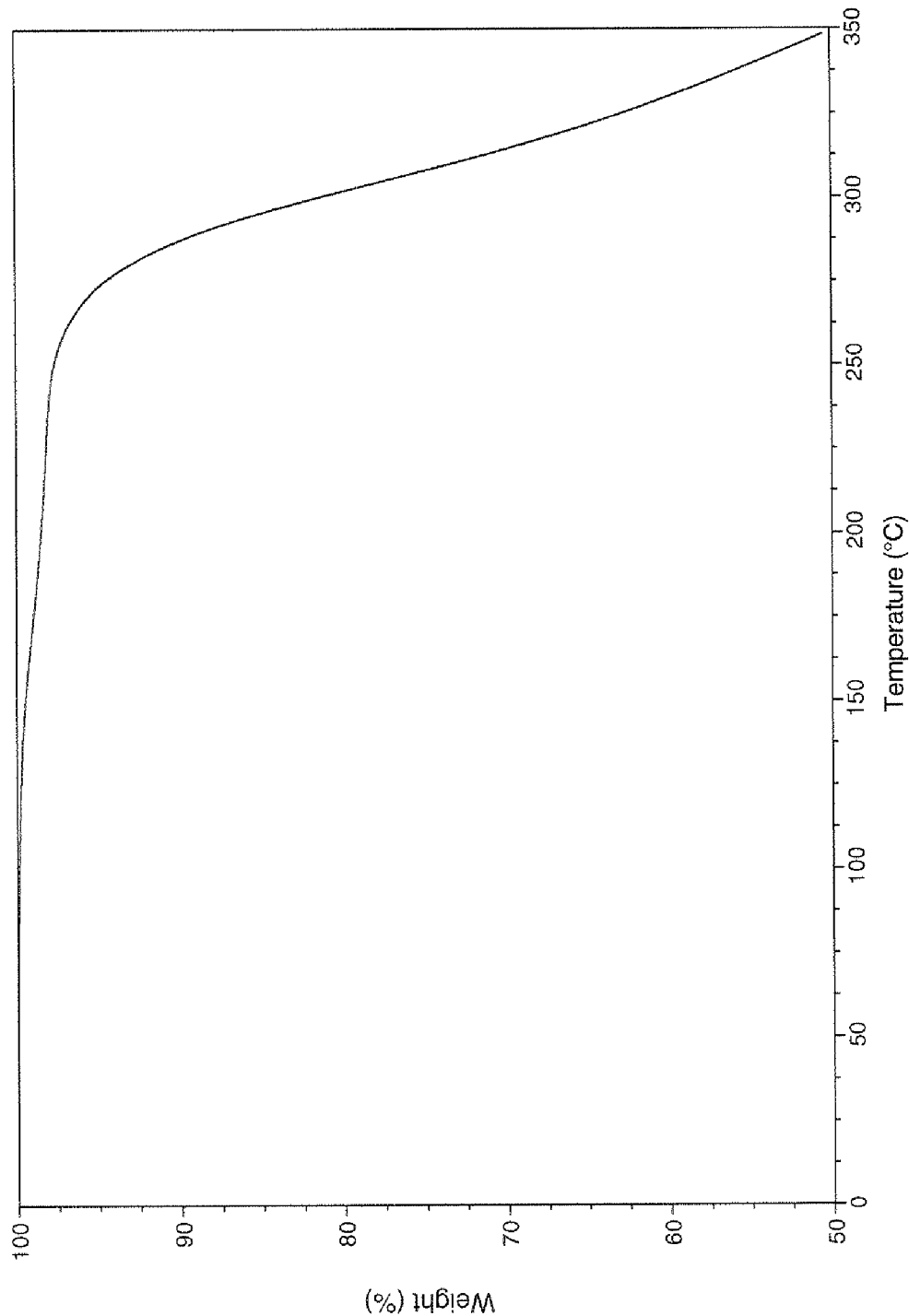
FIG. 4. is a graph of weight (percent) versus temperature (° C.) showing the results of thermogravimetric analysis of the Form F polymorph. The analysis was performed on a 3.4990 mg sample. Analysis was performed using a TA Instruments 2950 thermogrametric analyzer. Data were collected by heating under nitrogen at a rate of 10° C./min to a maximum temperature of 350° C.

The crystalline Sovaprevir of Form F has the characteristic 2θ values of FIG. 2.

The crystalline Sovaprevier form of Form F is characterized by an X-ray powder diffraction pattern obtained from a Cu Kα_source which comprises peaks at 2θ values of 4.2, 8.8, 13.0, and 19.9+/−0.2; or 9.7, 13.5, 14.9, 19.0, 19.6, 20.9, and 23.0+/−0.2; or 10.4, 17.1, 25.5, 26.1, 26.6, and 27.2+/−0.2.

The crystalline Sovaprevir of Form F has a melting point of 216° C. to 226° C.

The crystalline Sovaprevir of Form F has a primary endothem at 225° C. as determined by DSC.

EXAMPLES

Abbreviations

The following abbreviations may be useful when reviewing the schemes and examples of this disclosure.

DCM Dichloromethane
DIEA/DIPEA N,N-diisopropylethylamine
DMF Dimethyl formamide
DMSO Dimethyl Sulfoxide
DSC Differential Scanning calorimetry
EDC 1-Ethyl-3-(3-dimethylaminopropyl)carbodiimide
HATU (1-[Bis(dimethylamino)methylene]-1H-1,2,3-triazolo[4,5-b]pyridinium 3-oxid hexafluorophosphate)
HOBt Hydroxybenzotriazole
IPA Isopropyl Alcohol
KO$^t$Bu Potassium Butoxide
MeOH Methanol
MTBE Methyl tert-Butyl Ether
TBTU o-(Benzotriazol-1-yl)-N,N,N',N'-tetra methyluronium tetrafluoroborate
THF Tetrahydrofuran
TFA Trifluoroacetic Acid Example 1

Synthesis of (2S,4R)-1-((S)-2-(tert-butyl)-4-oxo-4-(piperidin-1-yl)butanoyl)-4-hydroxypyrrolidine-2-carboxylic acid (Compound C-1)

The synthesis of Compound C-1 is illustrated by Scheme IV. Examples 1-4 provide a complete method for synthesizing sovaprevir. This method is designated as Method 1.

Scheme IV

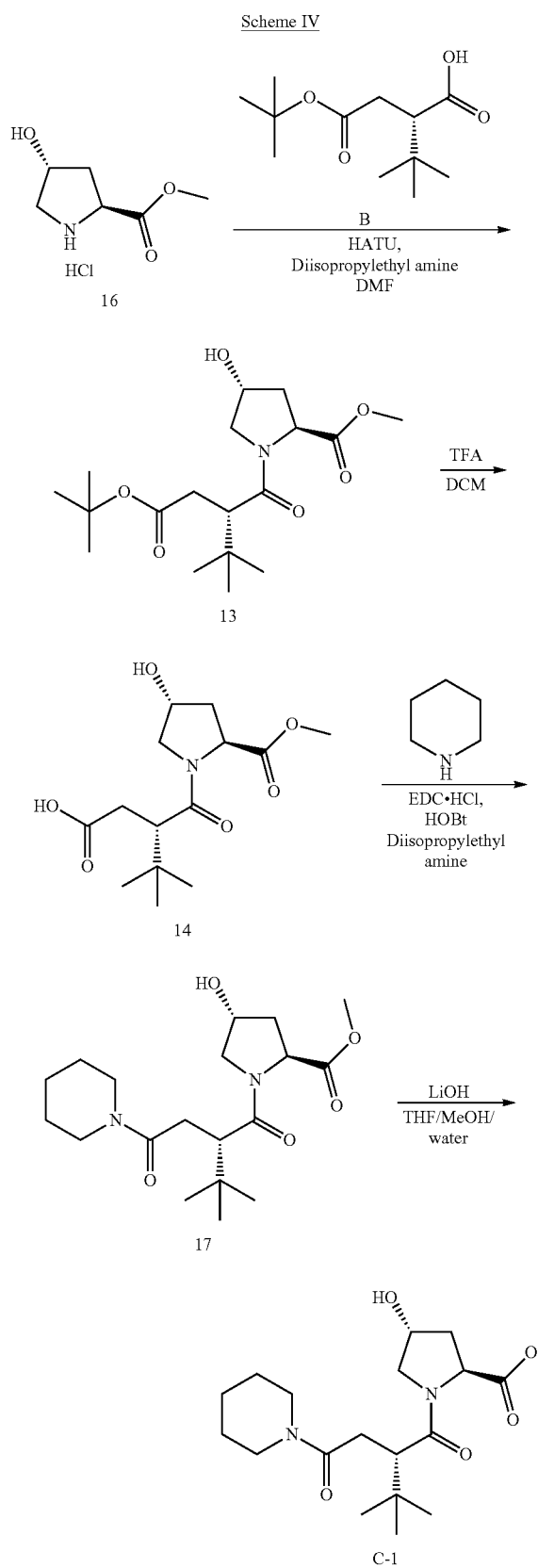

HATU (1.3 equivalent) was added to a mixture of hydroxyproline, 16 (1.5 equivalent), diisopropyl ethyl amine (5 equivalent) and acid B (1 equivalent) in dimethylformamide at a temperature between 5-25° C. The reaction was stirred for 15 h at room temperature, diluted with water and extracted with methyl t-butylether (MTBE). The organic layer was washed with 1M citric acid and brine. The organic layer was concentrated and residue crystallized from a mixture of MTBE/heptane to give compound 13.

Compound 13 was treated with trifluoroacetic acid in dichloromethane (2.3:5 v/v) to remove the t-butyl group. All the volatiles were removed and the material (compound 14) taken forward without purification to the next step.

Piperidine (1.2 equivalents) was added at ~5° C. to a solution of Compound 14, diisopropyl ethylamine (8.5 equivalents), EDC.HCl (1.3 equivalents), HOBt (0.14 equivalent) in dichloromethane. The reaction was stirred till completion at room temperature, diluted with dichloromethane, and washed with 1M citric acid followed by brine to give compound 17. Other peptide coupling agents may be used in place of EDC.HCl. These include N,N"-Dicyclohexylcarbodiimide (DCC), triazole coupling agents such as N,N,N',N'-etramethyl-O-(benzotriazol-1-yl)uronium tetrafluoroborate (TBTU), [Bis(dimethylamino)methylene]-1H-1,2,3-triazolo[4,5-b]pyridinium 3-oxid hexafluorophosphate (HATU), and benzotriazol-1-yl-oxytripyrrolidinophosphonium hexafluorophosphate (PyBOP), or pyridium coupling agents such as 2-Chloro-1-methylpyridinium iodide (Mukaiyama's reagent) and other peptide coupling agents well known in the art.

Compound 17 (1 equivalent) was dissolved in a mixture of THF/MeOH/water (4/0.17/1 v/v) and lithium hydroxide (1.2 equivalents) was added. The reaction was stirred till hydrolysis was complete (by HPLC). The reaction was evaporated to dryness, diluted with water and extracted with MTBE. The aqueous layer was acidified with HCl and extracted with dichloromethane. The organic layer was dried and concentrated and the residue crystallized from MTBE to give compound C-1.

Example 2

Synthesis of (1R)-1-amino-N-(cyclopropylsulfonyl)-2-vinylcyclopropanecarboxamide hydrochloride (Compound E)

Scheme V illustrates the synthesis of Compound E.

Scheme V

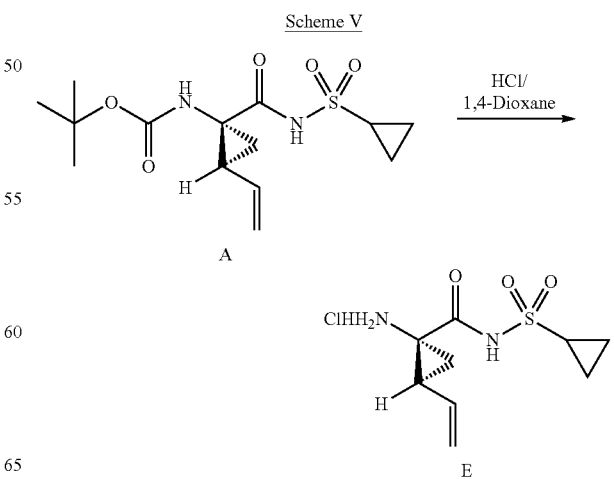

To a solution of compound A in 1,4-dioxane was added 4M HCl in dioxane and stirred for 3 h at room temperature. The reaction mixture was evaporated to dryness to give Compound E which was used for the next step without further purification.

Example 3

Synthesis of (2S,4R)-1-((S)-2-(tert-butyl)-4-oxo-4-(piperidin-1-yl)butanoyl)-4-((7-methoxy-2-phenylquinolin-4-yl)oxy)pyrrolidine-2-carboxylic acid (Compound F-1)

Scheme VI illustrates the preparation of Compound F-1.

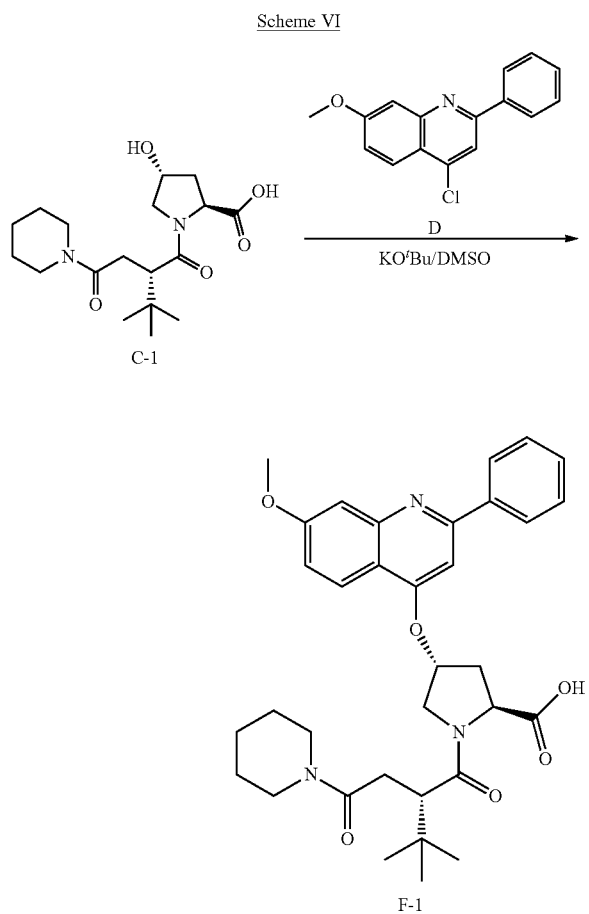

Potassium t-butoxide (2.5 equivalent) was added in portion to a solution of compound C-1 (1 equivalent) and the chloroquinoline D (1.0 equivalent) in dimethylsulfoxide and stirred for 24 h at room temperature. The reaction mixture was diluted with dichloromethane and washed with 1M citric acid and concentrated. The residue was triturated with MTBE and the solid isolated by filtration. The solid was crystallized from isopropyl alcohol, cooled to ~3° C. and filtered to give Compound F-1.

Example 4

Preparation of Sovaprevir

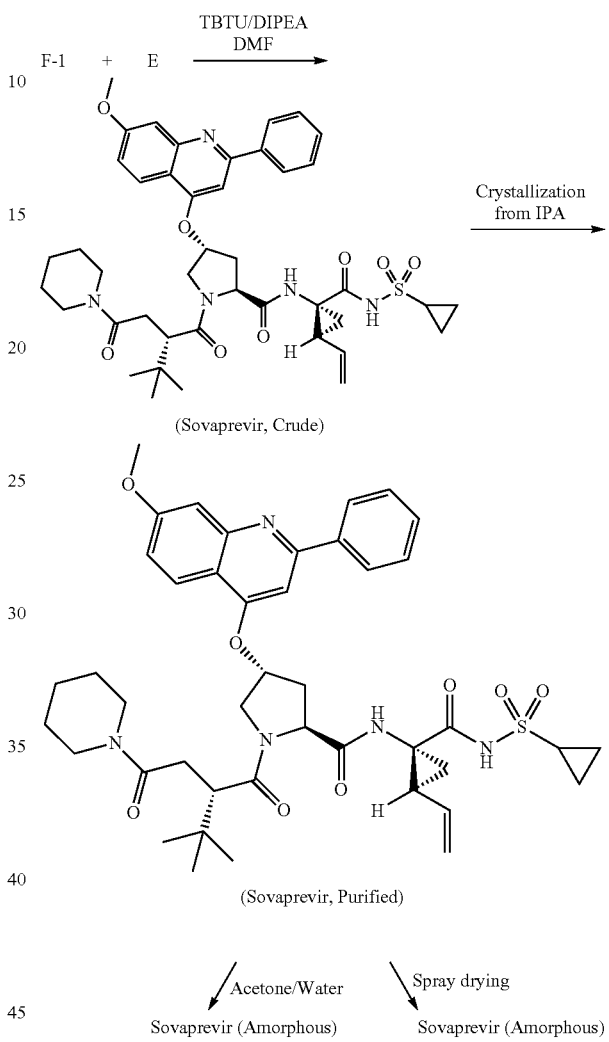

To a solution of Compound F-1 (1 equivalent), compound E (1 equivalent) and TBTU (1.3 equivalent) in dimethylformamide was added diisopropylethyl amine (5 equivalent) and stirred for 15 h at room temperature. The reaction mixture was diluted with ethylacetate, washed with 1M citric acid, 1M LiOH followed by 1M citric acid and brine. The solution is treated with charcoal and concentrated. The residue was triturated in hot heptane cooled and filtered to give Sovaprevir Crude. Sovaprevir Crude is crystallized from isopropyl alcohol to obtain purified Sovaprevir. Crystallizations from isopropyl alcohol (IPA) will generally produce a crystalline form that is soluble in acetone and typically crystalline Form F is produced.

Sovaprevir is amorphous in nature and is produced by precipitating a solution of Sovaprevir Purified in acetone into water. Sovaprevir purified is dissolved in 6-12 volumes of acetone and this solution is added to water (6.7 to 12 volumes in relation to acetone used) with vigorous stirring. The precipitated solid is filtered and dried to obtain sovaprevir.

Sovaprevir Purified is dissolved in acetone and spray dried to obtain amorphous Sovaprevir.

Example 5

Preparation of Sovaprevir (Method 2)

Schemes VIII through XIII illustrated the preparation of Sovaprevir by Method B.

Scheme VIII

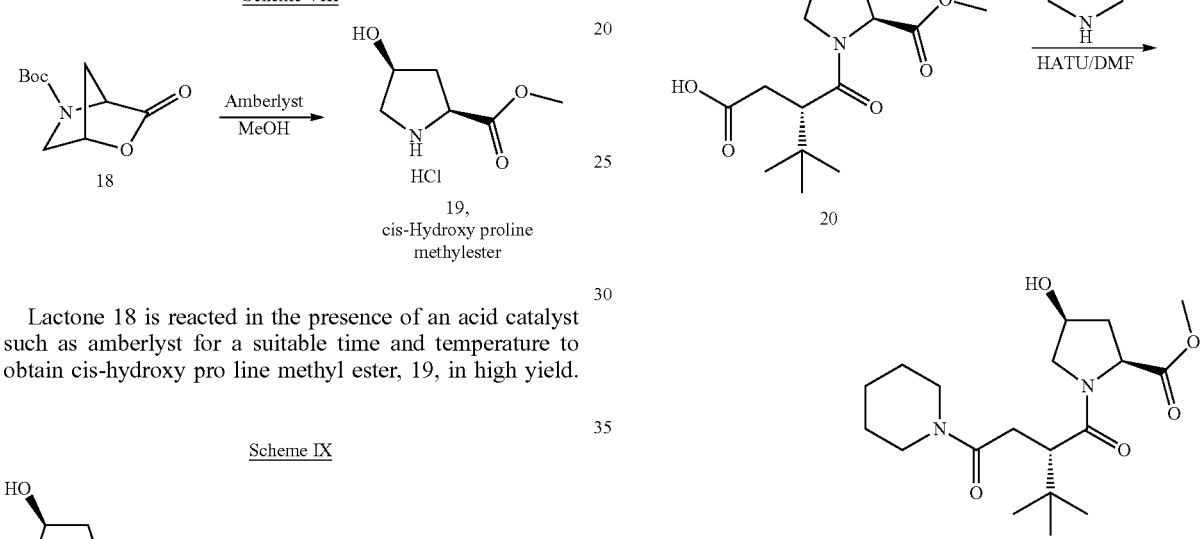

Lactone 18 is reacted in the presence of an acid catalyst such as amberlyst for a suitable time and temperature to obtain cis-hydroxy pro line methyl ester, 19, in high yield.

Scheme IX

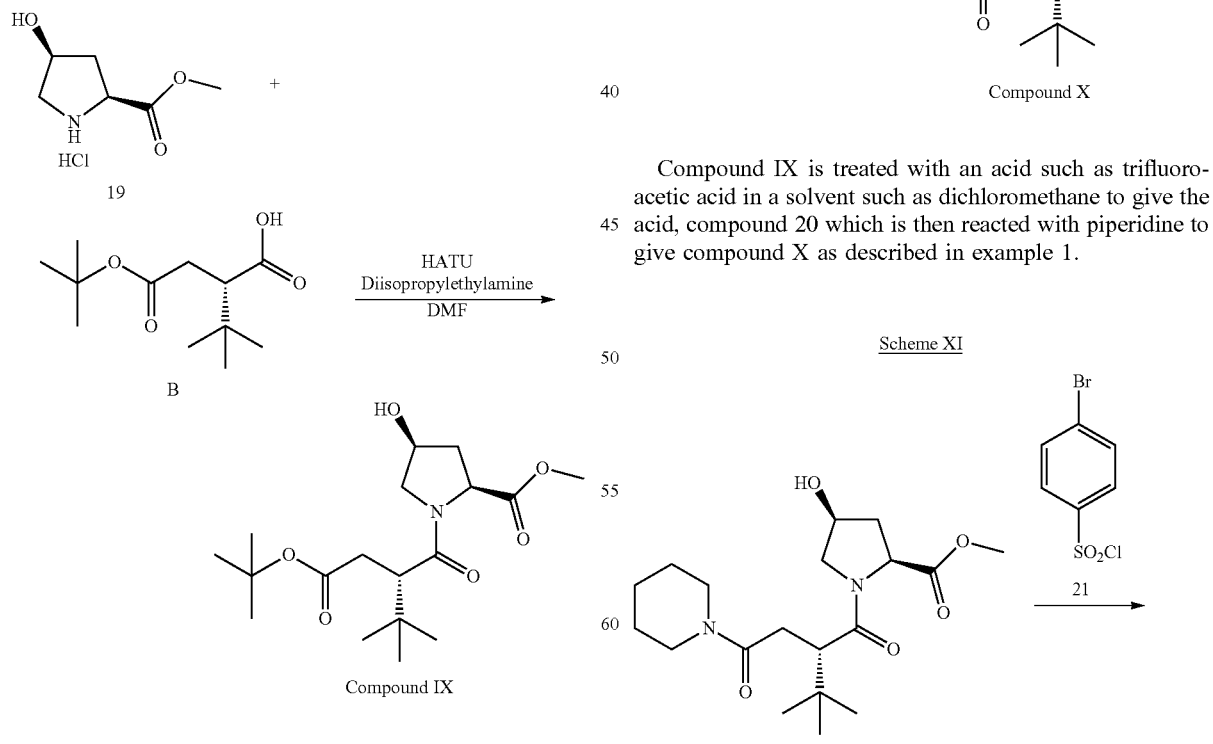

Cis-hydroxyproline methylester, 19, is reacted with compound B in presence of HATU and diisopropylethylamine in DMF to give compound IX as described in example 1.

Scheme X

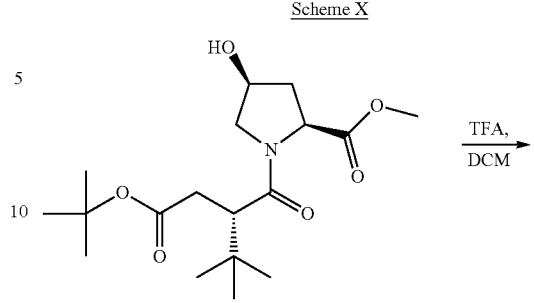

Compound IX is treated with an acid such as trifluoroacetic acid in a solvent such as dichloromethane to give the acid, compound 20 which is then reacted with piperidine to give compound X as described in example 1.

Scheme XI

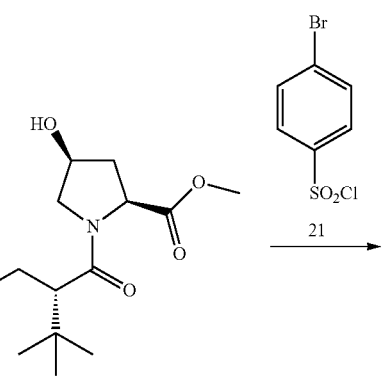

Compound X

19
-continued

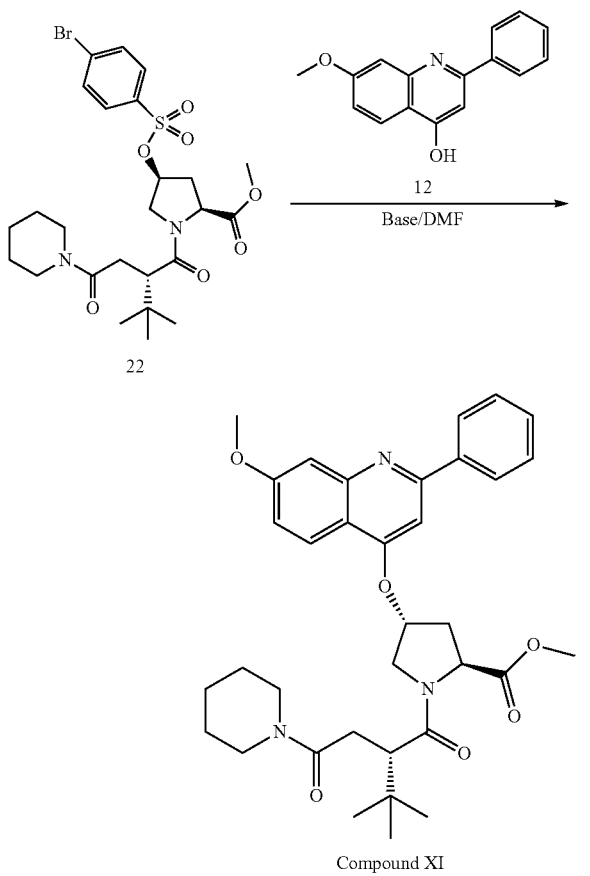

A solution of compound X is then reacted with Bromobenzene sulfonyl chloride (21) in presence of triethylamine and catalytic dimethylaminopyridine in solvent such as dichloromethane to obtain the brosylate (Compound 22) (methanesulfonyl chloride can also be used to make the mesylate), which can be used for the next step. The brosylate is then reacted with compound 12 in a solvent such as dimethylformamide in presence of a base such as potassium carbonate or potassium hydroxide or bases of the like to obtain compound XI.

Scheme XII

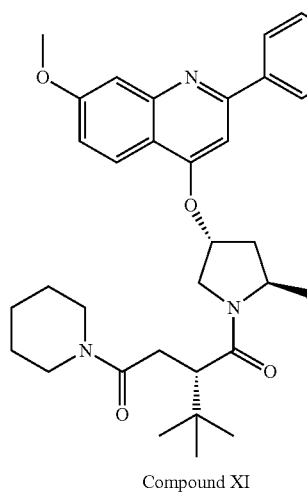

20
-continued

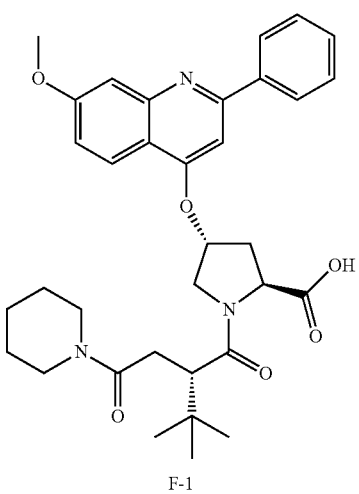

The ester group of compound XI is hydrolyzed to the carboxylic acid using a base such as lithium hydroxide in a solvent such as tetrahydrofuran and water to obtain compound F-1.

Scheme XIII

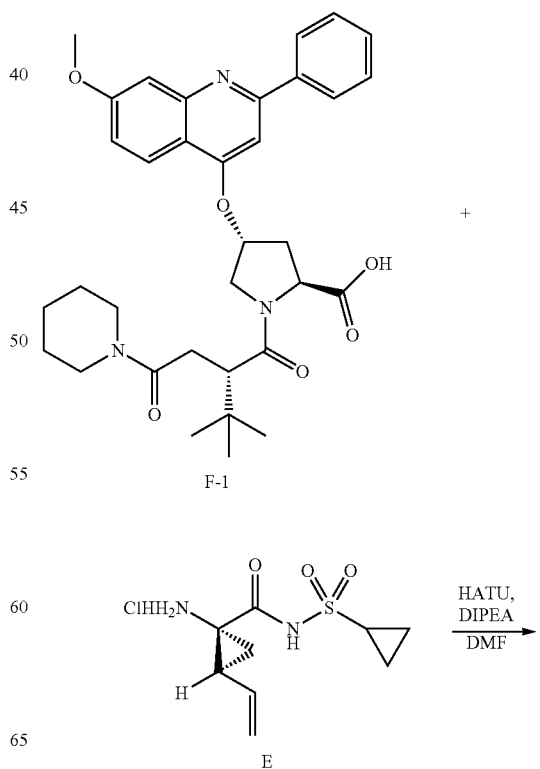

-continued

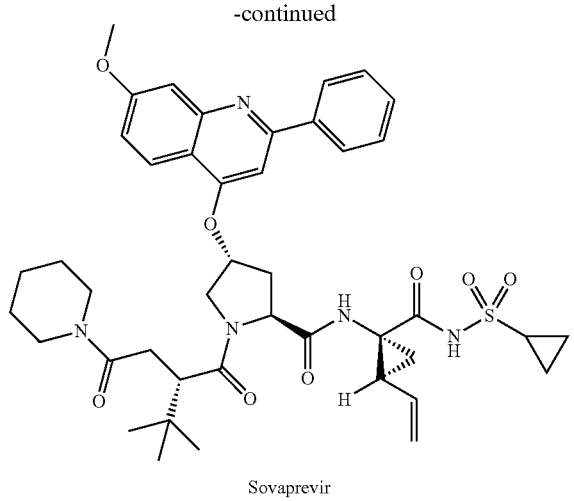

Sovaprevir

Compound F-1 is then treated with compound E as described in example 4.

Example 6

Crystallization of Polymorph F

Form F is crystallized from isopropanol. Form F was characterized by powder X-ray diffraction (pXRD), differential scanning calorimetry (DSC), thermogravimetric analysis (TG), and hot stage microscopy. The characterization results are presented in FIGS. 2-5.

XRPD patterns were collected using an Inel XRG-3000 diffractometer equipped with a curved position sensitive detector with a 2θ range of 120°. An incident beam of Cu Kα radiation (40 kV, 30 mA) was used to collect data in real time at a resolution of 0.03° 2θ. Prior to the analysis, a silicon standard (NIST SRM 640c) was analyzed to verify the Si 111 peak position. Samples were prepared for analysis by packing them into thin-walled glass capillaries. Each capillary was mounted onto a goniometer head and rotated during data acquisition. The monochromator slit was set at 5 mm by 160 μm, and the samples were analyzed for 5 minutes. Characteristic peaks are observed at the following 2θ values: 4.2, 8.8, 9.7, 10.4, 13.0, 13.5, 14.9, 17.1, 19.0, 19.6, 19.9, 20.9, 23.0, 25.5, 26.1, 26.6, and 27.2+/−0.2.

Differential scanning calorimetry (DSC) was performed using a TA Instruments differential scanning calorimeter Q2000. The sample was placed into an aluminum DSC pan, and the weight accurately recorded. The pan was covered with a lid and then crimped. The sample cell was equilibrated at −50° C. (or 25° C., depending on the sample) and heated under a nitrogen purge at a rate of 10° C./min, up to a final temperature of 250° C. Indium metal was used as the calibration standard. Reported temperatures are at the transition maxima.

Hot stage microscopy was performed using a Linkam hot stage (model FTIR 600) mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 20×0.40 N.A. long working distance objective with crossed polarizers and a first order red compensator. Images were captured using SPOT software (v. 4.5.9).

Termogravimetric analyses (TGA) were performed using a TA Instruments 2950 termogravimetric analyzer. Each sample was placed in an aluminum sample pan and inserted into the TGA furnace. The furnace was heated under nitrogen at a rate of 10° C./min, up to a final temperature of 350° C. Nickely and ALUMEL were used as the calibration standards.

Example 7

Characterization Data for Polymorph Form F

| Sample Source | Technique | Analysis/Result |
|---|---|---|
| lot 146-181-2, LIMS 188807, crystallized from dry IPA | XRPD | Form F |
| | DSC[a] | very minor broad endo 158, endo 225 (57 J/g) |
| | TG[b] | 1.59 @ 25-205° C. |
| | | 1.34 @ 125-205° C. |

[a]endo = endotherm, temperatures (° C.) reported are transition maxima. Temperatures are rounded to the nearest degree.
[b]weight loss (%) at a certain temperature; weight changes (%) are rounded to 2 decimal places; temperatures are rounded to the nearest degree.

What is claimed is:

1. A compound having the formula:

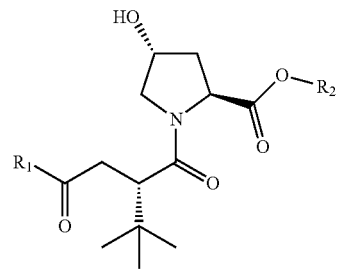

where
R$_1$ is C$_1$-C$_6$alkyl or hydroxyl, or R$_1$ is a 1-piperidinyl, 1-piperazinyl, or 1-pyrrolidinyl group, each of which is unsubstituted or substituted with 1 or 2 halogen substituents; and
R$_2$ is hydrogen or methyl.

2. A compound of claim 1 in which R$_1$ is t-butoxy, hydroxyl, or 1-piperidine, and R$_2$ is methyl.

3. A compound of claim 1 of the formula

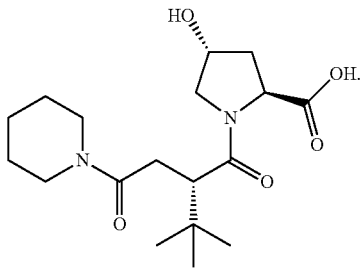 [SMILES: CC(C)(C)[C@H](CC(=O)N1CCCCC1)C(=O)N1C[C@H](O)C[C@H]1C(=O)O]

4. A compound of claim 1, having the formula of Compound IX

Compound IX

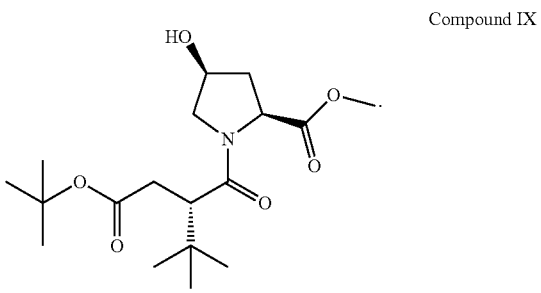 [SMILES: COC(=O)[C@@H]1C[C@H](O)CN1C(=O)[C@@H](CC(=O)OC(C)(C)C)C(C)(C)C]

5. A compound of claim 1, having the formula of Compound X
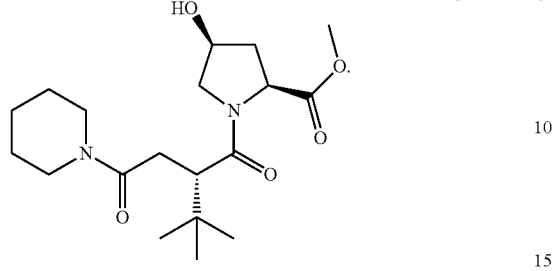
Compound X
* * * * *